United States Patent [19]

Black et al.

[11] Patent Number: 5,658,444
[45] Date of Patent: Aug. 19, 1997

[54] ELECTROCHEMICAL SENSORS

[75] Inventors: Murdo Black, Milton-Under-Wychwood; Long Lin; James Guthrie, both of Leeds, all of United Kingdom

[73] Assignee: MediSense, Inc., Bedford, Mass.

[21] Appl. No.: 545,805

[22] PCT Filed: May 11, 1994

[86] PCT No.: PCT/GB94/01011

§ 371 Date: Mar. 18, 1996

§ 102(e) Date: Mar. 18, 1996

[87] PCT Pub. No.: WO94/27140

PCT Pub. Date: Nov. 24, 1994

[30] Foreign Application Priority Data

May 12, 1993 [GB] United Kingdom ............... 9309797

[51] Int. Cl.[6] .................................................. G01N 27/26
[52] U.S. Cl. .......................... 204/415; 204/403; 204/295; 204/296; 435/969; 435/970; 435/975; 435/817; 422/61; 422/68.1; 422/73
[58] Field of Search .......................... 422/61, 62, 68.1, 422/73; 436/521, 532, 169, 170; 435/969, 970, 975, 817; 204/415, 403, 295, 296

[56] References Cited

U.S. PATENT DOCUMENTS

| | | | |
|---|---|---|---|
| 3,662,046 | 5/1972 | Woo et al. | 264/41 |
| 4,545,382 | 10/1985 | Higgins et al. | 128/635 |
| 5,055,195 | 10/1991 | Trasch et al. | 210/638 |
| 5,166,051 | 11/1992 | Killeen et al. | 422/61 |
| 5,262,067 | 11/1993 | Wilk et al. | 422/73 |
| 5,509,410 | 4/1996 | Hill et al. | 128/637 |

FOREIGN PATENT DOCUMENTS

| | | |
|---|---|---|
| 0 184 895 | 6/1986 | European Pat. Off. . |
| 0 230 786 | 8/1987 | European Pat. Off. . |
| 0 289 269 | 11/1988 | European Pat. Off. . |
| 0 325 413 | 7/1989 | European Pat. Off. . |
| 0 351 891 | 1/1990 | European Pat. Off. . |
| 0 415 679 | 3/1991 | European Pat. Off. . |
| 0 457 183 | 11/1991 | European Pat. Off. . |
| 0 127 958 | 3/1992 | European Pat. Off. . |
| 0 475 692 | 3/1992 | European Pat. Off. . |
| 3323973 | 1/1985 | Germany . |

OTHER PUBLICATIONS

Search Report PCT/GB94/01011.

*Primary Examiner*—Bruce F. Bell
*Attorney, Agent, or Firm*—Fish & Richardson P.C.

[57] ABSTRACT

Erythrocyte exclusion membranes suited for test strips of electrochemical sensors have a porous matrix and a mobile erythrocyte aggregating agent. The membranes typically comprise a water-insoluble hydrophobic polymer incorporating a hydrophilic polymer and with the erythrocyte aggregating agent. Such membranes can have a pore size which is several times larger than the diameter of erythrocytes, and allow rapid passage of plasma by holding back the erythrocytes as rouleaux at the surface of the membrane. The membranes are preferably made by forming in situ on a test strip using spray casting.

29 Claims, 3 Drawing Sheets

ELECTROCHEMICAL SENSORS

RELATED APPLICATION

This is a continuation of PCT application PCT/GB94/01011 filed May 11, 1994.

INTRODUCTION

The present invention relates to electrochemical sensors, and more particularly but not exclusively to electrochemical biosensors. The present invention further relates to a method of manufacture of test strips for use in such sensors.

BACKGROUND OF THE INVENTION

There is an increasing public awareness of the diagnostic significance of levels of components in the blood and other body fluids, and many sensors are designed for non-expert use. A particular goal is the provision of electrochemical sensors which do not require elaborate preparation of a test sample, and can rapidly give a result merely by application of the body fluid to a test strip. Good sensitivity is achieved usually with a biochemically specific reaction, such as by enzymatic catalysis of a reaction of the component to be detected. The reaction results in transfer of charge which can be qualitatively or quantitatively detected, for instance by an amperometric procedure.

Amperometric biosensors for performing diagnostic tests for components of body fluids are described, for example, in U.S. Pat. No. 4,545,382, European Patent 127958 and European Patent 351891. Such devices offer the facility for rapid, convenient and specific measurements of analyte components in blood by lay users, and a sensor for glucose is commercially available as the MediSense® ExacTech® sensor.

Whole blood is a complex, predominately aqueous mixture containing dissolved gases, simple dissociated and hydrated ions, materials in colloidal or other form of solution, small scale cellular debris, and living cellular components including red blood cells, the erythrocytes. It is sometimes difficult to achieve reproducible analytical results with electrochemical sensors when using whole blood samples. Variations in red cell concentration, the haematocrit, is the main contributor to inaccuracies in using whole blood samples for electrochemical sensors.

Accordingly, there is a need to develop improved electrochemical sensors which are less dependent on the haematocrit of the blood. To this end, there have been proposals for overlay membranes which serve to exclude erythrocytes so that the sensor itself is only contacted by blood plasma. Illustrative examples of proposals for erythrocyte exclusion membranes are to be found in published EP-A 289269 and other patent literature.

There are difficulties in developing a satisfactory erythrocyte exclusion membrane suited for test strips such as amperometric electrode test strips. A human erythrocyte is deformable in vivo to pass through luminal diameters as small as 2 or 3 μm, and thus membranes of this porosity are ineffective, either because the erythrocytes leak through by deformation or because the erythrocytes plug the pores to prevent passage of the plasma. Where the porosity is further reduced, the transport of plasma is difficult. In this respect, the typical volume of the blood sample for an amperometric glucose test is only 20 μl and yet gravity has to provide the principal driving force, with capillary forces providing only a secondary driving force. Given the goal of maintaining or reducing measurement times, where the period for a complete glucose test is typically 30 seconds, rapid transport of the plasma through the membrane is needed.

Thus, the transport of the plasma requires an open membrane structure, while the separation of erythrocytes demands a closed membrane structure. In the light of these contradictory requirements, it becomes clear that conventional membrane systems are not entirely suitable.

U.S. Pat. No. 5,055,195 describes the use of retention substrates which bring about strong coagulation of blood so that the corpuscular components are effectively retained in a paper or glass fibre fleece and are separated from the plasma. This object is achieved by using retention substrates which contain two strongly polar groups which are connected by a non-polar bridge. The retention substrates are preponderantly dyestuffs, and they bring about random clumping.

OBJECTS OF THE INVENTION

An object of the present invention is provide an improved erythrocyte exclusion membrane for an electrochemical sensor. In this respect, it is an object to provide an improved porous erythrocyte exclusion membrane which permits rapid transport of plasma through the membrane, while substantially excluding the passage of erythrocytes. A particular object is the provision of a disposable single-use electrode test strip for an amperometric biosensor, for use with a sample of whole blood, which is less dependent on the haematocrit of the blood.

A related object is to provide a new method for the manufacture of test strips.

SUMMARY OF THE INVENTION

According to the present invention, there is provided an erythrocyte exclusion membrane comprising a porous matrix including an erythrocyte aggregating agent.

The erythrocyte aggregating agent is an agent which can induce the formation of erythrocyte aggregates known as rouleaux. Such rouleaux have a diameter of typically 50 to 100 times that of an individual erythrocyte, and are not random clumps. Accordingly, with the inclusion of the erythrocyte aggregating agent, the porosity of the membrane can be such that individual erythrocytes might otherwise pass through the matrix, but rouleaux can not pass through the matrix. The erythrocyte aggregating agent is present at or migrates to the surface of the membrane to bring about formation of the rouleaux. In this way, the erythrocytes are held outside the membrane pores, allowing effective transport of the plasma with separation from the erythrocytes.

Thus, the present invention provides a test strip for an electrochemical sensor for contact with whole blood in order to effect an electrochemical measurement. The test strip has an exclusion layer in the form of a porous membrane with an erythrocyte aggregating agent. The membrane excludes red blood cells from contact with the sensing electrodes by aggregating them at the surface of the membrane and excluding them as erythrocyte rouleaux. By virtue of the presence of the exclusion layer, the, sensing electrodes are exposed only to plasma, so that the red blood cells can not interfere. In this way, reproducible results are more easily achieved, even for disposable test strips made in high volume and at low cost.

PREFERRED EMBODIMENTS

The preferred porous matrix of the polymeric membrane mainly consists of a water-insoluble hydrophobic polymer so that this matrix will not be significantly altered by the water present in whole blood. However, membranes consisting of such material have poor wetting ability. In order to obtain effective plasma transport through the membrane pores, the porous hydrophobic matrix preferably incorporates a hydrophilic polymer.

A preferred membrane thus comprises at least three groups of polymeric materials, namely a hydrophobic polymer, a hydrophilic polymer, and a mobile erythrocyte aggregating agent.

The hydrophobic polymer is a water-insoluble but organic solvent-soluble membrane-forming polymer which provides the desired porous membrane structure. Such polymers are well known and typically contain hydrophobic functional groups at a dominant level, though a minor proportion of hydrophilic functional groups can be present. Examples of the hydrophobic polymer include cellulose acetate propionate, cellulose acetate, polyvinyl butyral, polystyrene, etc.

The hydrophilic polymer is a water-soluble and organic solvent-soluble polymer which provides good membrane permeability to plasma and especially dissolved analytes in the plasma. Such polymers are well known and typically contain hydrophilic functional groups at a dominant level, though a minor proportion of hydrophobic functional groups can be present. Examples of the hydrophilic polymer include hydroxypropyl cellulose, polyvinylpyrrolidone, polyvinyl alcohol, polyvinyl acetate, etc.

The erythrocyte aggregating agent is suitably a water-soluble and organic solvent-soluble component, typically polymeric, which can easily be released and dissolved into blood plasma when it is brought into contact with the blood. Such a material induces and accelerates erythrocyte aggregation as rouleaux at the surface of the membrane, thus preventing the erythrocytes from passing through the membrane. Examples of the erythrocyte aggregating agent which act as a mobile erythrocyte aggregating agent include dextran and positively charged polymers such as polylysine salts, polybrene (that is, hexadimethrine bromide), protamine, etc. It is preferred that the erythrocyte aggregating agent is more soluble in water than the hydrophilic polymer, in order that the erythrocyte aggregating agent is the first component to dissolve and can rapidly induce formation of the rouleaux.

The relative amounts of the three components are chosen on the basis of the desired properties of the membrane such as the porosity and hydrophobicity. A preferred range for the weight ratio (hydrophobic polymer):(hydrophilic polymer) is from 3:1 to 1:3, more preferably from 2:1 to 1:2, and most preferably from 3:2 to 2:3. Thus, the typical membrane contains about equal mounts of the two types of polymer.

The erythrocyte aggregating agent is usually a minor component of the membrane, and preferably comprises from 5 to 45% of the membrane, more preferably from 10 to 40% and most preferably from 25 to 35%. Thus, the typical membrane contains about 30% of the erythrocyte aggregating agent.

Other components may be included in the membrane, such as surfactants to improve wetting, or plasticizers such as dioctyl phthalate.

In the preferred membrane there is a generally homogenous distribution of heterogenous polymeric components with the mobile erythrocyte aggregating agent located inside a polymeric network of interconnecting porous pathways through the membrane. In preferred embodiments, the pore diameters are in the range 1 to 15 µm, more preferably 3 to 15 µm. One of the features of this invention which distinguishes this membrane system from other membranes is the characteristic of separating erythrocytes from whole blood even when the pore size of the membrane is significantly lager than the maximum diameter of the erythrocytes.

A proposed mechanism for erythrocyte separation by the preferred membrane is described as follows, though we are not bound by this theory. After whole blood is brought into contact with the membrane, the plasma wets across the membrane surface and soaks into the hydrophilic polymer, making it swell to reduce the membrane pore size. At this initial stage, the erythrocytes are held outside the membrane pores, transport of plasma through the membrane is relatively slow, and the erythrocyte aggregating agent is mobilized and forced out from the membrane pores into the plasma. The mobile erythrocyte aggregating agent has high solubility in the aqueous phase and dissolves into the plasma faster than the hydrophilic polymer, initiating the formation of rouleaux. The plasma then wets through the hydrophilic material to give more swelling and to release more erythrocyte aggregating agent which accelerates the process of erythrocyte rouleaux formation, to stop the erythrocytes from penetrating the membrane. When most of the erythrocyte aggregating agent has dissolved, the hydrophilic material starts to dissolve into the plasma, effectively opening up the membrane pores to allow faster transport of the plasma. At this stage, the size of the membrane pores may be larger than that of an individual erythrocyte, but by this time most erythrocytes have become erythrocyte rouleaux and the membrane is therefore still capable of holding the erythrocytes outside the membrane pores to prevent fouling of the membrane pores which occurs with most of the conventional procedures for membrane separation.

The membranes of the present invention are especially suited for use in electrode test strips for an electrochemical sensor. Such a sensor, for example for amperometric or potentiometric detection, typically employs a dry throwaway electrode test strip. The electrodes preferably comprise electrode areas formed for instance by screen printing or other suitable technique. Reference is made to EP-A 127958, 184895, 230786, among other published European Patent Specifications in the name of MediSense, Inc., formerly known as Genetics International Inc., and the disclosures of these three European Patent Specifications are incorporated for their teaching of manufacturing methods and constructional features. The membrane of this invention for an amperometric electrode test strip usually has a thickness in the range 20 to 50 µm.

The membrane is preferably formed in situ on the strips. As an example of the in situ procedure, the membrane can be made by spray casting. With casting, the membrane will be formed in intimate contact with the strip surface. There are other advantages in casting or coating of the polymer solution directly on the strip surface by spraying a polymer solution followed by evaporation of the solvents. With such a technique, it is possible to control the porosity of the membrane, notably by selection of solvents and spraying conditions. Moreover, the possibility of deactivating the enzymes can be greatly reduced, since unlike dip-coating the polymer solution reaching the electrode surface contains lower levels of solvents.

The membrane components are dissolved in a mixed solvent and mixed thoroughly. Depending on the characteristics of the polymeric materials, the membrane casting techniques and the desired membrane morphology, different solvent systems are used. The polymers, the mixed solvent system, the mixing ratio and the membrane deposition method and conditions are usually selected so that a membrane is obtained which is characterised by its homogeneity and the uniform distribution of micropores, preferably within the size range 1 to 15 μm. The porosity will typically reflect the spraying distance, the spray pressure, and the volatility of the solvents. In particular, larger pores are produced as the spraying distance is reduced, and, correspondingly, smaller pores are produced as the spraying distance is increased. The thickness of the membrane can be controlled as desired and depends on the polymeric materials, the concentration of these materials in the continuous medium and the manufacturing conditions.

The resultant preferred membrane structure is distinguished by the distribution of three polymeric components. The hydrophobic polymer forms the porous structure, and the other polymers coat the surface of this structure. In this way, the blood sample spreads rapidly over the membrane. The rapid transport is facilitated by the porous structure and hydrophilic properties of the surfaces. In other words, the hydrophillic functional groups facilitate the wetting of the surface while the micropores provide a path for the diffusing constituents.

Techniques apart from spray casting can be used. For instance, the membrane can be separately made as a sheet for fixing to strips during manufacture of the strips. As an example of the separate sheets, the membrane can be made by dip coating of a porous support, for example a mesh such as nylon mesh, or a web of non-woven polyester. The porosity will typically reflect the relative amounts of the membrane components, the choice of solvent, and processing such as water-rinsing. The polymeric components can be sprayed or applied by inkjet or pulsejet printing, needle dosing, rollercoating, printing, and similar techniques.

Membrane solutions can be cast onto the tranquil surface of a bath of non-solvent for the membrane polymers. A polymeric membrane forms when solvents evaporate from the membrane solution. The final membrane is obtained by removing the polymeric membrane from the non-solvent bath and drying it in air.

Membrane solutions can also be cast onto the surface of glass plate to allow the solvents to evaporate into the air. A polymeric membrane is obtained when most solvents evaporate. The dried membrane can easily be detached from the glass plate with the help of a silicon spray on the glass plate before casting.

Membrane solutions can also be directly cast onto the object surface using printing techniques.

THE DRAWINGS

The invention will be further described by way of example with reference to FIGS. 1 to 6 of the accompanying drawings, in which.

Figure 1:
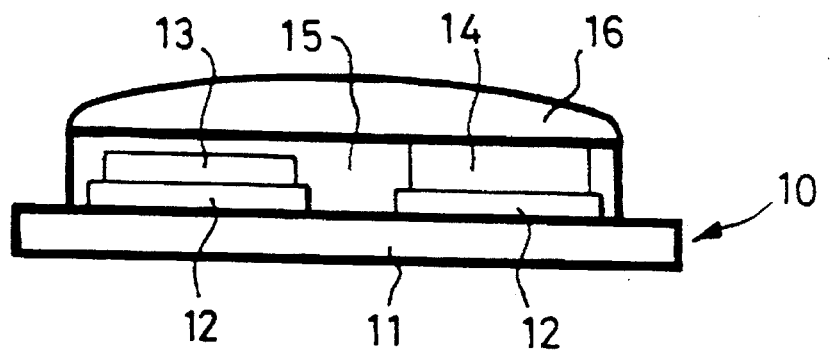
FIG. 1 shows in diagrammatic cross-section a first embodiment of the invention.

FIG. 1 shows a dry disposable electrode test strip 10 for use as part of an amperometric test sensor. A PVC substrate 11 carries carbon tracks 12 overlain with silver tracks and coated to form a working electrode 13 and a reference electrode 14 which are covered by a membrane 15. The carbon tracks form contacts for connection of the strip to readout apparatus, and are coated with a silver conductive ink to improve the conductivity of the carbon. In use, a drop of blood 16 is applied to the surface of the membrane.

Figure 2:
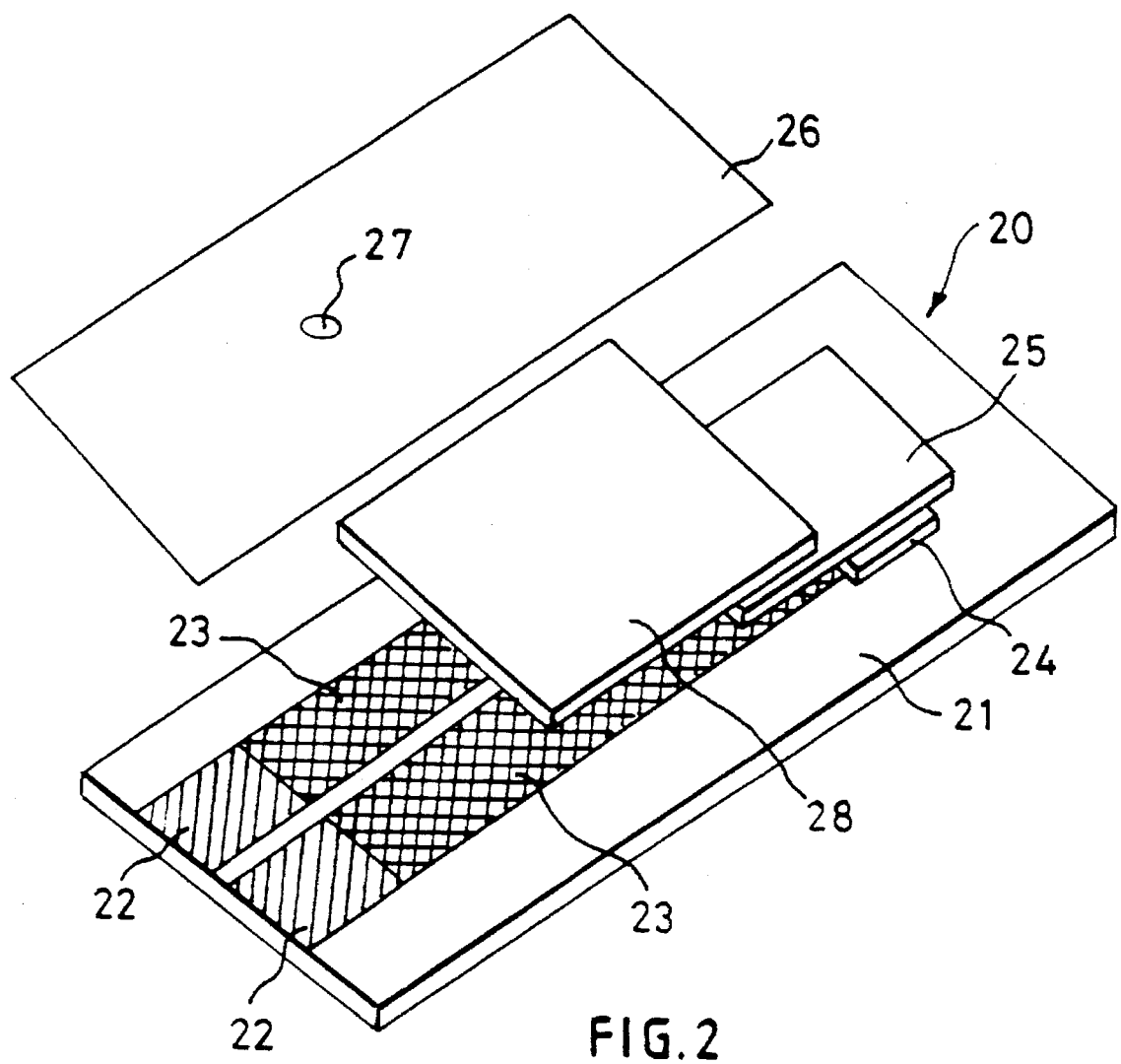
FIG. 2 shows an exploded perspective view of a second embodiment.

FIG. 2 shows a second embodiment of the invention. A PVC substrate 21 of a test strip 20 carries carbon tracks 22 overlain with silver tracks 23 and coated to form a working electrode 24 and a reference electrode (not visible) which are covered by a membrane 25. In this case the test strip 20 has an outer coat 26 as a non-porous humidity barrier. An aperture 27 in the humidity barrier forms a target sample application zone, for the application of whole blood. Blood applied to zone 27 wicks under coat 26 through a permeable material 28 to membrane 25 where plasma components rapidly penetrate and wet the electrodes.

The configuration of FIG. 2 not only acts as a barrier to red blood cells, but also reduces the effect of environmental factors on the strip response.

Figure 3:
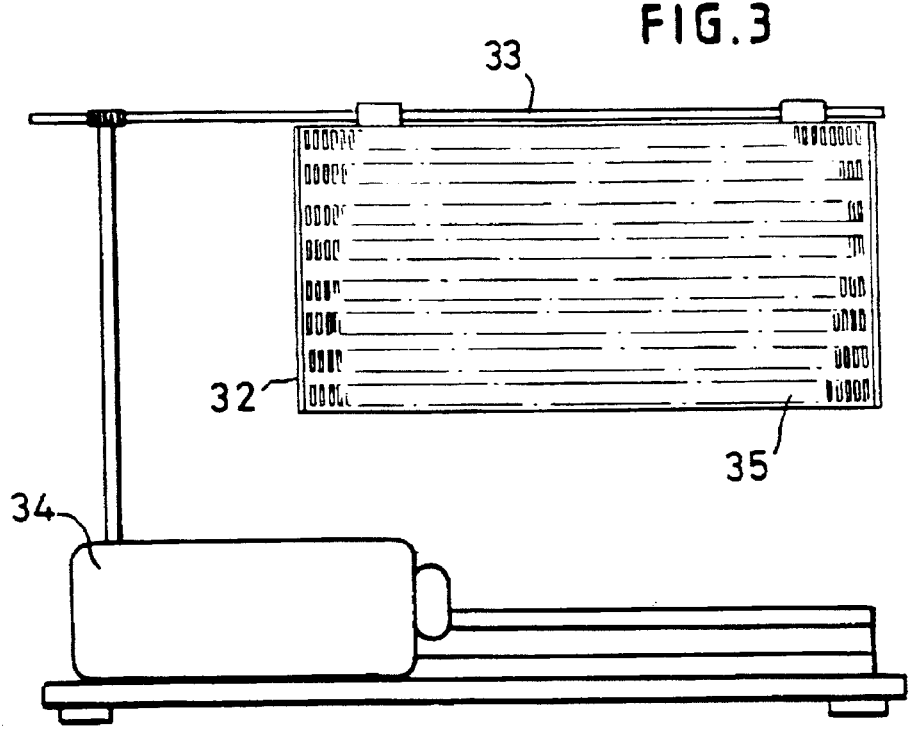
FIGS. 3 and 4 shows apparatus for spray casting employed in the Examples.
Figure 4:
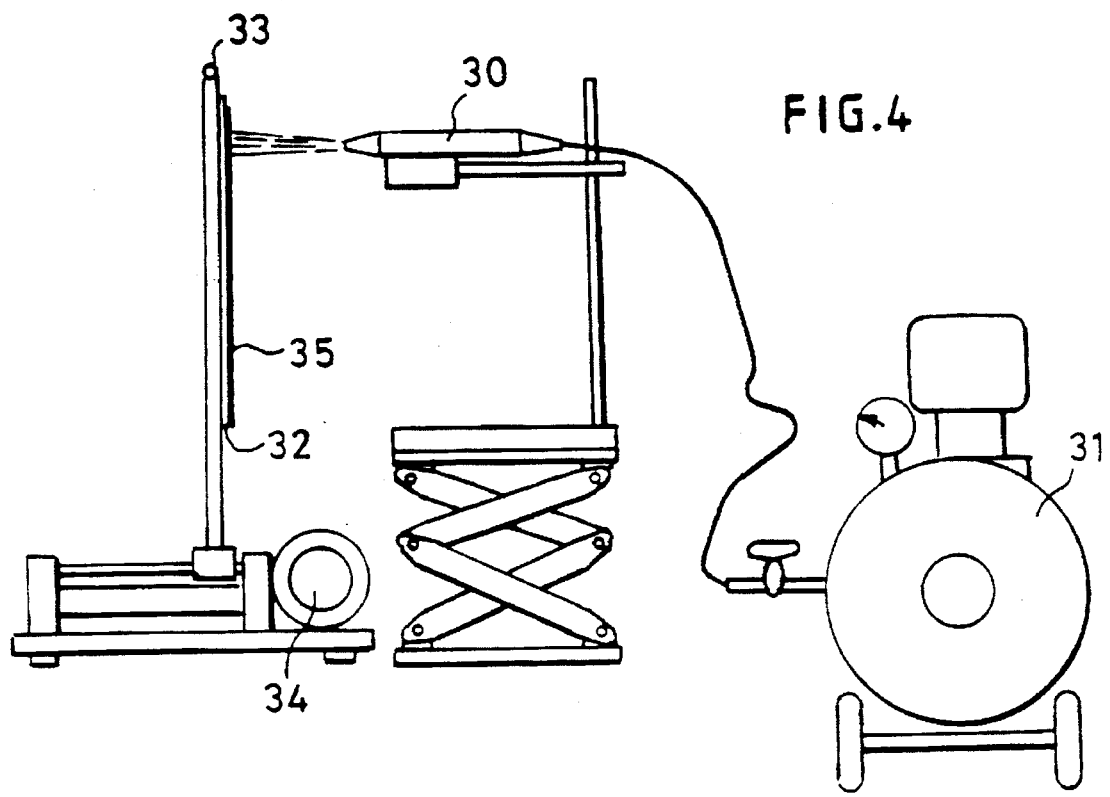

In FIGS. 3 and 4, apparatus for spray casting of the membranes employs an air brush 30, driven from a compressor 31. In this instance, the air brush 30 was stationary and a card 32 of multiple electrode strips was mounted on a metal rail 33 driven by an adjustable motor 34. The electrode card 32 was covered by a stencil 35 to give deposition of the membrane polymer solution onto the intended electrode sensing area.

Figure 5:
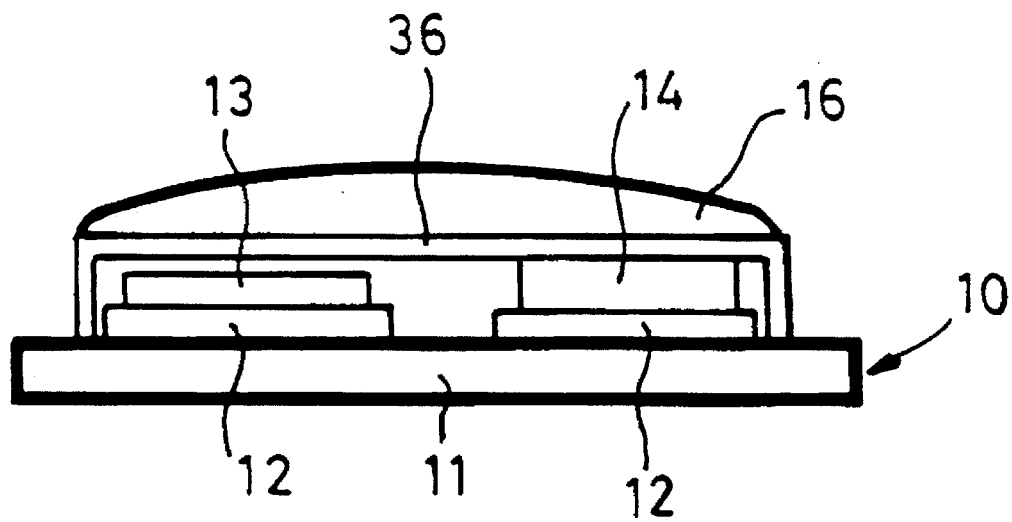
FIG. 5 shows in diagrammatic cross-section a third embodiment of the invention.

In the embodiment of FIG. 5, the construction is as shown m FIG. 1, except for the provision of the membrane in the form of a nylon mesh 36 dip-coated with polymer solution.

Figure 6:
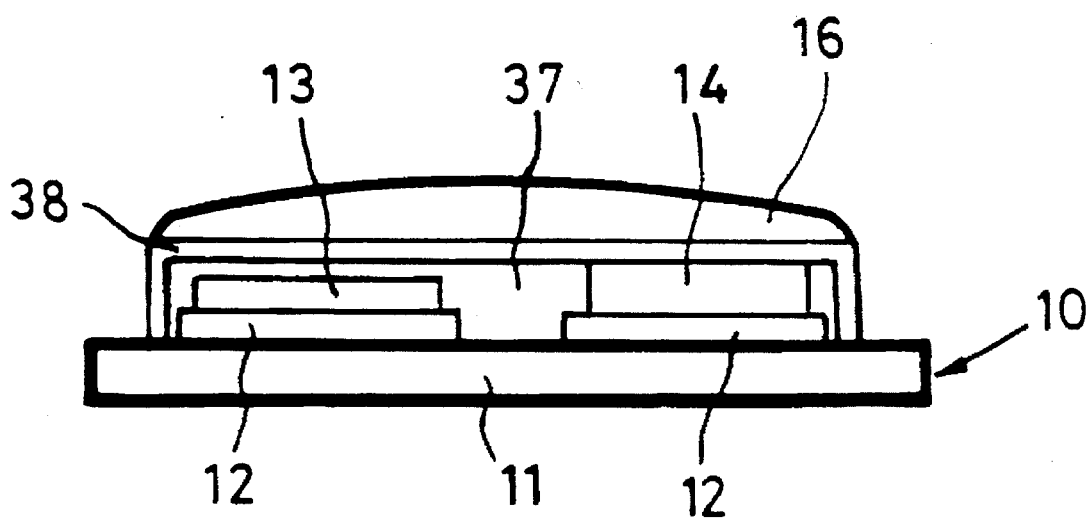
FIG. 6 shows in diagrammatic cross-section a fourth embodiment of the invention.

In the embodiment of FIG. 6, the construction is as shown m FIG. 1, except for the provision of the membrane as two polymer layers 37, 38.

EXAMPLES OF THE INVENTION

Example 1

Electrode test strips for cholesterol were made in accordance with EP-A 230786, using screen printing. In this manufacturing process, multiple electrodes were screen printed onto a large sheet of carrier material, which was then subdivided to give individual test strips. The screen-printing process comprises the following steps;

a) printing of a conductive tracking b) printing of a working electrode c) printing of a reference electrode, and d) printing of a dielectric insulation.

The working electrode was prepared from commercially obtained horse radish peroxidase, cholesterol oxidase, cholesterol esterase, sodium cholate and binder. These were reconstituted in an imidazole buffer mix of pH 7 for 2 hours prior to the addition of finely divided carbon and 1,1'-dimethylferrocene ethanolamine as mediator. The working electrode was screen printed onto the preprinted carbon track. The mix was allowed to dry.

Batches of the electrode test strips were provided with membranes in accordance with the present invention. The resultant electrodes conformed with the construction shown in FIG. 1. The conductive carbon tracking for each electrode was screen-printed onto the surface of the substrate in two conductive tracks of 45 mm by 2 mm, with a separation of 3 mm. The membrane was spray coated over the electrodes. Where desired, the test strips can be with the construction shown in FIG. 2, with a surfactant coated nylon mesh as permeable material 28 and a humidity overlayer 26 applied over the membrane.

For the spray-casting of the membrane, polymer solutions were spray-cast onto the surface of the electrodes as part of the manufacturing process.

The step of spray-casting was carried out using the apparatus of FIGS. 3 and 4, with an air brush (Badger Model 200, Badge Air-Brush Co., Illinois), driven from an oil-free air compressor (Pioneer 200, Clark International, London). The distance between the spray nozzle of the air-brush 30 and the electrode card 32 and the vertical position of air-brush 30 was set up to be easily adjusted, it being recognised that this distance affects the evaporation of solvent and thus the structure of the cast membrane. The typical spray-casting parameters used for the membrane coating were as follows:

| | |
|---|---|
| Distance between the spray nozzle and the targeted electrode surface: | 18 cm |
| Electrode movement: | 125 cm/min |
| Number of spray passes: | 2 |

A number of polymeric materials were investigated for their suitability as the membrane materials for the membranes. The following polymeric materials showed particularly promising characteristics:

Hydrophobic polymer:

Cellulose acetate propionate (CAP Eastman Chemicals, Kingsport, Tenn., USA)

Poly(vinyl butyral) (B-72 or B-79, Butvar, Monsanto Ltd., St. Louis, Mo., USA)

Hydroxyethyl cellulose (Natrosol 250 mR, Aqualon UK Ltd., Chester, UK)

Hydrophilic polymer:

Hydroxypropyl cellulose (Klucel HPC L, Aqualon UK Ltd., Chester, UK)

Poly(vinyl alcohol) (Aldrich Chemicals Co. Ltd., Gillingham, Chester, UK)

Erythrocyte aggregating agent:

Dextran 3759 (Sigma Chemical Co. Ltd., Poole, Dorset, UK)

Ethyl acetate was found to be a possible solvent. However, CAP/HPC solutions in ethyl acetate have a milky appearance and a second solvent is needed, in order to provide an entirely miscible polymer solution containing CAP/HPC. Ethanol and methanol were found to suitable. Methanol gives a true solution of CAP/HPC at a much smaller presence in the solvent mixture than does ethanol. It was ascertained that the optimal amount of methanol in the polymer solution was 8%. This amount of methanol when combined with 82% of ethyl acetate, 5% of CAP and 5% of HPC gives a clear solution of CAP/HPC with low viscosity and good processability.

Appropriate amounts for a 5% solution of each of the polymers CAP and HPC were added to the solvent mixture in a ball-milling jar. Complete solution of the polymers in the solvent mixture took about 30 minutes under stirring. An appropriate amount of dextran was milled in a mortar to reduce the particle size to around 50 μm and then mixed into the polymer solution. This mixture was then milled with ceramic milling balls until the dextran particle size fell below 20 μm. In the resultant polymer mixture, the ratio CAP:HPC:dextran was 3.6:3.6:0.7. Initially, this mixture too high a viscosity for spray application, and the polymer solution/composition was then diluted with ethyl acetate/methanol (90%/10%). The coatings were deposited onto the electrode surfaces using the equipment. The membranes were then dried. The performance of the membrane-coated cholesterol electrodes were then assayed.

Drawing on this initial work, polymer solutions containing various compositions of CAP, HPC, dextran, ethyl acetate and methanol were prepared. These polymer solutions were cast onto the sensing area of cholesterol electrodes. In general with the spray procedure, there was some difficulty in achieving reproducible homogenous coating.

From this work, the optimal formulation, which gave the best membrane morphology and membrane transport performance, is given in the following table.

| Materials | Composition(%) |
|---|---|
| CAP | 3.6 |
| HPC | 3.6 |
| Dextran | 0.7 |
| Ethyl acetate | 82.8 |
| Methanol | 9.3 |

The resultant membrane had an average pore size of 4 μm, as determined by scanning electron microscopy.

In a side experiment, the formulation was spray coated onto filter paper and dried. A stainless steel weight with a drilled 4 mm central hole was put on the filter paper. The membrane-coated paper with weight were placed on a sheet of uncoated filter paper. A 15 μl blood sample was added to the hole and left for 15 seconds. The underlying uncoated filter paper was then evaluated for erythrocyte breakthrough, and found to be straw coloured. This result indicates that only plasma passed through the membrane, with the main driving force being gravity.

In order to study the transport properties of the membrane cast on the electrode surface, membrane-coated electrodes were evaluated using blood samples. A range of blood samples with haematocrits varying between 30% and 60% PCV (packed cell volume) and constant cholesterol were tested. Electrodes were either uncoated, or coated with of membrane either 5 μm or 10 μm thick.

The i-t transients were recorded and integrated over 40 to 60 seconds. The following data for different batches of electrodes were obtained:

| | Haematocrit regression -v-μC response | | |
|---|---|---|---|
| | slope | regression | CV (%) |
| uncoated | −0.355 | 0.817 | 2.56 |
| coated (5 μm) | 0.026 | 0.029 | 8.86 |
| coated (5 μm) | −0.076 | 0.227 | 2.74 |
| coated (10 μm) | −0.018 | 0.056 | 3.22 |
| coated (10 μm) | 0.015 | 0.023 | 6.9 |

All of the electrodes with the membrane thus gave a negligible haematocrit effect.

Example 2

It was found that the morphology of the membranes of Example 1 was sometimes sensitive to the parameters associated with the spray operation. Considering that an optimized industrial process needs relatively low sensitivity to the process parameters, alternative membrane formulations were designed.

A solvent blend which contains acetone, methanol and mesitylene was found to be more suitable. Acetone and methanol were used as solvents for CAP and HPC respectively. Acetone evaporates first into the air when the membrane solutions are cast onto the electrode surface. As a result of this acetone evaporation, CAP in the membrane solution is transformed from a gel-phase into a solid phase. The solid-phase CAP forms the skeleton of the membrane structure. The precipitation of HPC is slower than that of CAP because HPC is retained in methanol which evaporates slower than acetone. Therefore, the CAP-acetone system gives a primary porous structure. The HPC deposits on the surface of the primary membrane pores.

Mesitylene was used as a pore-former in the membrane. Mesitylene is a non-solvent to the CAP, HPC and dextran. Mesitylene has a much higher boiling point than either acetone or methanol. Thus, it remains in the membrane for a longer time than acetone or methanol. This enables mesitylene to be a good former of secondary membrane pores.

A typical formulation for a membrane solution is as follows:

| Cellulose Acetate Propionate | 1.25% | POLYMER 1 |
| Klucel Hydroxypropyl Cellulose | 1.25% | POLYMER 2 |
| Dextran MW 87,000 g/mol | 0.25% | POLYMER 3 |

Surfactant (Fluorad FC170C, 3M Company Commercial Chemicals Division, St. Paul, Minn., USA)

| | 0.25% |
| Acetone | 43.5% |
| Methanol | 43.5% |
| Mesitylene | 10.0% |

The resultant membrane when using a spraying distance of 4.0 cm had an average pore size of 7 µm, as determined by scanning electron microscopy.

Apart from cellulose acetate propionate, there are many hydrophobic polymers with good solubility in organic solvents which can be used as the POLYMER 1 in the membrane formulation. These polymers include cellulose acetate, polyvinyl butyral, polystyrene, etc.

Alternatives to the hydroxypropyl cellulose, which can be used as the POLYMER 2 and have good solubility in organic solvents include polyvinylpyrrolidone, polyvinyl alcohol, polyvinyl acetate, etc.

There are alternative polymers apart from dextran, which can be used as POLYMER 3 in the membrane formulations. These polymers should have high molecular weights, good hydrophilicity and should be soluble in organic solvents. Some positively charged polymers with good hydrophilicity and with modest to good solubility in organic solvents can also be used. These alternatives to dextran include polylysine, polybrene, protamine, etc.

Example 3

The main advantage of plasma separation is a reduction in the red cell interference on the sensor electrodes. This interference is due to diffusional limitation and some interfering reaction. With increasing haematocrit there is a reduction response at the sensor electrode at a constant analyte concentration. With an effective red cell exclusion membrane a reduced haematocrit response is expected.

Electrode test strips for glucose were made in accordance with EP-A 127958, using screen printing. The manufacturing process was much the same as that described in Example 1 for the manufacture of electrode test strips for cholesterol, except that the working electrode was prepared from commercially produced glucose oxidase and binder. These were reconstituted in BES buffer pH 7.4 for 2 hours prior to addition of ultrafine carbon and 1,1'-dimethylferrocene ethanolamine as mediator.

Batches of the strips were sprayed at different distances with the formulation of Example 2 to form membranes of different pores sizes. The following results for glucose sensors in accordance with EP-A 127958, with and without membranes, show the relative reduction in haematocrit response, corrected for glucose sensitivity.

| | Spraying Distance (cm) | Membrane Pore Size (µm) | Relative Haematocrit Response (%) |
|---|---|---|---|
| Uncoated electrodes | | | 100 |
| Membrane coated electrodes | 3.5 | 10 | 45.4 |
| Membrane coated electrodes | 4.0 | 7 | 23.3 |
| Membrane coated electrodes | 5.5 | 2 | 33.1 |

In this experiment the 7 µm pore size membrane gave the greatest reduction in relative haematocrit sensitivity.

Example 4

The dip-coating technique was also used to produce membranes for test strips for glucose sensors in accordance with EP-A 127958. The construction of the resultant test strip is illustrated in FIG. 5.

Nylon mesh was dipped into the polymer solutions to allow the nylon mesh to be coated with the polymer solution. The coated nylon mesh was then removed from the polymer solution and allowed to dry. These procedures gave a uniform polymeric membrane on the nylon mesh. In fine-tuning the membrane morphology, rinsing and then washing of the dip-coated nylon mesh with water, to give more porous membrane morphology was carried out.

A typical polymer solution used for dip-coating the nylon mesh is given below, and contained CAP, HPC, tetrahydrofuran (THF), cyclohexanone and dioctyl phthalate. In this solution, CAP, the major membrane material, formed the rigid skeleton of the membrane system. HPC contributed to the formation of microporous structure and to the hydrophilicity of the membrane system. By altering the ratio of CAP and HPC in the polymer solution, it is possible to control the porosity of the membrane structure. THF is the major solvent used in the polymer solution. THF plays an important role in inducing the formation of a microporous membrane structure. Under the experimental conditions, it was found that the evaporation rate of the THF was high, and there was some difficulty in obtaining membranes of uniform thickness. Cyclohexanone was used as a minor solvent for CAP and for HPC. By altering the ratio of the THF and cyclohexanone, the solvent evaporation rate was controlled to a satisfactory degree to achieve a membrane of accurate thickness. The porosity increased with increasing amounts of cyclohexanone. Dioctyl phthalate was used to provide plasticity to the membrane structure. This was because a membrane consisting of CAP and HPC can be brittle. Dioctyl phthalate was chosen in this context because its physicochemical nature allows it to assist the diffusion of plasma through the membrane.

Nylon mesh was dipped for a few seconds into the polymer solutions. The mesh was then rinsed with water at ambient temperature for 5 seconds to induce the precipitation of CAP and the extraction of part of the HPC from the membrane assembly. The system was then dip-coated with a mixture of 1% dextran, 1% surfactant and water at ambient temperature, and dried in air. In the dip-coating technique used in this study, the water rinse was designed to induce the precipitation of CAP and to dissolve part of the HPC contained in the cast polymer solution, to improve the efficiency of plasma transport. The water rinse helps the formation of the porous structure in the membrane, to provide desired hydrophilicity. The coated nylon mesh was then fixed onto the electrode surface of both the cholesterol electrodes and the glucose electrodes.

Polymeric materials were investigated for their suitability as ingredients in a dip-coating formulation. A preferred dip-coating membrane formulation was found to be as follows:

| Polymer | % | |
|---|---|---|
| CAP | 2 | Polymer 1 |
| HPC | 2 | Polymer 2 |
| THF | 85 | Solvent 1 |
| Cyclohexanone | 4 | Solvent 2 |
| Dioctyl phthalate | 7 | Additive |

The surface morphology of a typical dip-coated nylon mesh membrane was examined by scanning electron microscopy, showing porous structures with an average pore size of 4 μm.

Screen printed sensors for cholesterol were prepared in accordance with EP-A 230786, with and without the dip-coated membrane.

On testing, it was found that the cholesterol electrodes with membrane gave higher electrode currents than the cholesterol electrodes without membrane, and higher values i-t integration.

From statistical analysis of the data, it was concluded that the membrane cholesterol electrodes have higher sensitivity to the cholesterol than do the ordinary cholesterol electrodes. This is indicated by the higher slope of cholesterol calibration line for the membrane cholesterol electrodes (10.539) than that for the ordinary cholesterol electrodes (5.412).

Tests for the haematocrit effect were carried out on the ordinary cholesterol electrodes and the cholesterol electrodes covered with dip-coated membranes in order to evaluate the ability of the membrane to separate erythrocytes from blood samples. The blood samples were as follows:

Sample 1: Haematocrit level=36% Cholesterol concentration=6.98 mM.

Sample 2: Haematocrit level=44% Cholesterol concentration=6.98 mM.

Sample 3: Haematocnt level=54% Cholesterol concentration=6.98 mM.

The i-t transients were obtained and integrated over the period 27–40 seconds, in order to carry out haematocrit effect analysis. The average statistical parameters for the tested batch associated with the haematocrit effect lines are given in the next table.

| Electrode Type | Slope | $\delta_s$ | Intercept | $\delta_i$ | R |
|---|---|---|---|---|---|
| No Membrane | −0.137 | 0.051 | 21.725 | 2.306 | 0.5982 |
| Membrane | −0.072 | 0.124 | 19.648 | 5.478 | 0.2510 |

From the table, it can be concluded there is a reduced haematocrit effect using the dip-coated nylon meshes. There is a reduction of the absolute value of the slope of the haematocrit effect lines from 0.137 (for the ordinary cholesterol electrodes) to 0.0721 (for the membrane-treated cholesterol electrodes).

Example 5

Dextran has limited solubility in many organic solvents. Another approach to the inclusion of dextran in the membrane assemblies is spray-casting of a two-layer, membrane assembly. The idea involves spray-casting a polymer solution containing CAP and HPC as the first membrane layer followed by spray-casting a polymer solution containing dextran on top of the first membrane layer. The construction of the resultant test strip is illustrated in FIG. 6.

The hydrophobic polymer and the hydrophilic polymers can be prepared for the casting of the first membrane layer. The erythrocyte aggregating agent material, dextran, can be dissolved in ethylene glycol to give the polymer solution for the casting as the second membrane layer. Polymer solutions either containing both HPC and dextran were prepared. Since ethylene glycol has too low a volatility, a mixture of ethanol and ethylene glycol was used as the solvent in preparation of the solution for the second membrane layer.

Membranes with different contents of dextran were prepared. These membranes consisted of two membranes layers each approximately 5 to 10 μm in thickness. The first membrane layer contained 50% of CAP and 50% of HPC. The second membrane layer consisted of dextran and HPC. The composition of dextran in the second layer was varied to allow assessment of the function of dextran in the separation of erythrocytes. The formulations of the polymer solution for casting of the second membrane layer are given in the next table. These polymer solutions contain 90% of ethylene glycol.

| | Compositions (%) | |
|---|---|---|
| Solutions | Dextran | HPC |
| 1 | 0.0 | 10.0 |
| 2 | 2.5 | 7.5 |
| 3 | 5.0 | 5.0 |
| 4 | 7.5 | 2.5 |
| 5 | 10 | 0.0 |

The cholesterol electrodes, coated with the CAP/HPC (50%:50%, first layer) and dextran/HPC (second layer), were tested for their efficiency in separating erythrocytes and in transporting cholesterol.

Whole human blood samples were used, as follows:

Sample 1: Haematocrit level=32%

Sample 2: Haematocrit level=34%,

Sample 3: Haematocrit level=48%.

The i-t transients were integrated over the period of 15–30 seconds, and from the SD values, it can be concluded that the i-t transients obtained have satisfactory overall reproducibility.

The haematocrit effect lines were plotted, giving the following data.

| Dextran (%) | Slope | $\delta_s$ | Intercept | $\delta_i$ | R |
| --- | --- | --- | --- | --- | --- |
| 0.0 | −0.427 | 0.045 | 30.055 | 1.886 | 0.984 |
| 2.5 | −0.156 | 0.048 | 20.028 | 1.971 | 0.916 |
| 5.0 | −0.003 | 0.141 | 17.350 | 5.751 | 0.010 |
| 7.5 | −0.044 | 0.120 | 18.987 | 4.899 | 0.180 |
| 10.0 | −0.052 | 0.025 | 14.360 | 1.040 | 0.822 |

These results shown the ability of dextran to facilitate the exclusion of erythrocytes, as demonstrated by the decrease in absolute value of the slopes from 0.427 to 0.003.

We claim:

1. An erythrocyte exclusion membrane for a sensor, said membrane comprising a porous polymeric matrix including a water-insoluble hydrophobic polymer and a water-soluble hydrophilic polymer in said matrix, wherein said porous matrix comprises pores of pore diameters in the range of 1 to 15 μm, said membrane further comprising a water-soluble erythrocyte aggregating agent.

2. The membrane of claim 1, said hydrophobic polymer, said hydrophilic polymer and said erythrocyte aggregating agent comprising a single layer.

3. The membrane of claim 1, comprising first and second layers, said first layer comprising said porous matrix and said second layer including said erythrocyte aggregating agent.

4. The membrane of claim 1, further including a porous support.

5. The membrane of claim 1, wherein said hydrophobic polymer is selected from the group consisting of cellulose acetate propionate, cellulose acetate, polyvinyl butyral and polystyrene.

6. The membrane of claim 1, wherein said hydrophilic polymer is selected from the group consisting of hydroxypropyl cellulose, polyvinylpyrrolidone, polyvinyl alcohol and polyvinyl acetate.

7. The membrane of claim 1, wherein said erythrocyte aggregating agent is a mobile erythrocyte aggregating agent selected from the group consisting of dextran, polylysine salts, hexadimethrine bromide, and protamine.

8. The membrane of claim 1, wherein said erythrocyte aggregating agent is more water-soluble than said water-soluble hydrophilic polymer.

9. The membrane of claim 1, wherein the pores of said porous polymeric matrix have pore diameters in the range 3 to 15 μm.

10. The membrane of claim 1 wherein said hydrophobic polymer is selected from the group consisting of cellulose acetate propionate, cellulose acetate, polyvinyl butyral and polystyrene, said hydrophilic polymer is selected from the group consisting of hydroxypropyl cellulose, polyvinylpyrrolidone, polyvinyl alcohol and polyvinyl acetate, and said erythrocyte aggregating agent is a mobile erythrocyte aggregating agent selected from the group consisting of dextran, polylysine salts, hexadimethrine bromide, and protamine.

11. The membrane of claim 10 in which the weight ratio of said hydrophobic polymer to said hydrophilic polymer is from 3:1 to 1:3.

12. The membrane of claim 11, said hydrophobic polymer, said hydrophilic polymer and said erythrocyte aggregating agent comprising a single layer, said erythrocyte aggregating agent comprising 5 to 45% of said membrane.

13. The membrane of claim 12 wherein said erythrocyte aggregating agent is more water soluble than said water soluble hydrophilic polymer.

14. The membrane of any one of claims 10 to 12 wherein the pores of said polymeric matrix have pore diameters in the range of 3 to 15 μm.

15. The membrane of claim 14 wherein said erythrocyte aggregating agent is more water soluble that said water soluble hydrophilic polymer.

16. A test strip for an electrochemical sensor for contact with whole blood in order to effect an electrochemical measurement, said test strip having an exclusion membrane in the form of a porous polymeric membrane, said membrane comprising a porous polymeric matrix including a water-insoluble hydrophobic polymer and a water-soluble hydrophilic polymer, wherein said porous matrix comprises pores of pore diameters in the range of 1 to 15 μm, said membrane further comprising a water-soluble erythrocyte aggregating agent.

17. The test strip of claim 16, which is an amperometric test strip having electrode areas overlain by said exclusion layer.

18. The test strip of claim 16, wherein said exclusion layer has a thickness in the range 20 to 50 μm.

19. The test strip of claim 16, wherein said hydrophobic polymer is selected from the group consisting of cellulose acetate propionate, cellulose acetate, polyvinyl butyral and polystyrene.

20. The test strip of claim 16, wherein said hydrophilic polymer is selected from the group consisting of hydroxypropyl cellulose, polyvinylpyrrolidone, polyvinyl alcohol and polyvinyl acetate.

21. The test strip of claim 16, wherein said erythrocyte aggregating agent is a mobile erythrocyte aggregating agent selected from the group consisting of dextran, polylysine sales, hexadimethrine bromide, and protamine.

22. The test strip of claim 16, wherein said erythrocyte aggregating agent is more water-soluble than said water-soluble hydrophilic polymer.

23. The test strip of claim 16, wherein the pores of said porous polymeric matrix have pore diameters in the range of 3 to 15 μm.

24. The test strip of claim 16, wherein said hydrophobic polymer is selected from the group consisting of cellulose acetate propionate, cellulose acetate, polyvinyl butyral and polystyrene, said hydrophilic polymer is selected from the group consisting of hydroxypropyl cellulose, polyvinylpyrrolidone, polyvinyl alcohol and polyvinyl acetate, and said erythrocyte aggregating agent is a mobile erythrocyte aggregating agent selected from the group consisting of dextran, polylysine salts, hexadimethrine bromide, and protamine.

25. The test strip of claim 24 in which the weight ratio of said hydrophobic polymer to said hydrophilic polymer is from 3:1 to 1:3.

26. The test strip of claim 25, said hydrophobic polymer, said hydrophilic polymer and said erythrocyte aggregating agent comprising a single layer, said erythrocyte aggregating agent comprising 5 to 45% of said membrane.

27. The test strip of claim 26, wherein said erythrocyte aggregating agent is more water-soluble than said water-soluble hydrophilic polymer.

28. The test strip of any one of claims 24 to 26, wherein the pores of said polymeric matrix have pore diameters in the range of 3 to 15 μm.

29. The test strip of claim 28, wherein said erythrocyte aggregating agent is more water-soluble than said water-soluble hydrophilic polymer.

* * * * *